(12) United States Patent
Noda et al.

(10) Patent No.: US 8,802,917 B2
(45) Date of Patent: Aug. 12, 2014

(54) ABSORBENT ARTICLE AND SANITARY NAPKIN

(75) Inventors: Yuki Noda, Kanonji (JP); Kenichiro Kuroda, Kanonji (JP); Shinpei Komatsu, Kanonji (JP)

(73) Assignee: Uni-Charm Corporation, Ehime (JP)

( * ) Notice: Subject to any disclaimer, the term of this patent is extended or adjusted under 35 U.S.C. 154(b) by 859 days.

(21) Appl. No.: 12/994,814

(22) PCT Filed: May 25, 2009

(86) PCT No.: PCT/JP2009/059516
§ 371 (c)(1),
(2), (4) Date: Feb. 28, 2011

(87) PCT Pub. No.: WO2009/145138
PCT Pub. Date: Dec. 3, 2009

(65) Prior Publication Data
US 2011/0144605 A1    Jun. 16, 2011

(30) Foreign Application Priority Data
May 28, 2008  (JP) ................................ 2008-140055

(51) Int. Cl.
| | | |
|---|---|---|
| *A61F 13/15* | (2006.01) | |
| *A61F 13/511* | (2006.01) | |
| *A61F 13/84* | (2006.01) | |
| *A61F 13/475* | (2006.01) | |
| *A61F 13/539* | (2006.01) | |
| *A61L 15/42* | (2006.01) | |
| *A61F 13/42* | (2006.01) | |
| *A61F 13/534* | (2006.01) | |

(52) U.S. Cl.
CPC ........... *A61F 13/42* (2013.01); *A61F 13/51104* (2013.01); *A61F 13/8405* (2013.01); *A61F 2013/8426* (2013.01); *A61F 13/4756* (2013.01); *A61F 13/539* (2013.01); *A61L 15/42* (2013.01); *A61F 13/534* (2013.01)
USPC ........................................................ 604/361

(58) Field of Classification Search
CPC ............................ A61F 13/42; A61F 2013/421
USPC ..................... 604/361, 380, 385.04, 385.101
See application file for complete search history.

(56) References Cited

U.S. PATENT DOCUMENTS 5,649,914 A  *  7/1997  Glaug et al. ................. 604/361
5,681,298 A     10/1997  Brunner et al.

(Continued)

FOREIGN PATENT DOCUMENTS

| EP | 1338262 A1 | 8/2003 |
| EP | 1813235 A2 | 8/2007 |

(Continued)

OTHER PUBLICATIONS

Office Action issued Apr. 22, 2013 in the corresponding Egyptian Patent Application No. 2010111994.

(Continued)

*Primary Examiner* — Lynne Anderson
(74) *Attorney, Agent, or Firm* — Lowe Hauptman & Ham LLP

(57) ABSTRACT

An absorbent article comprises a liquid-permeable top sheet, a liquid-impermeable back sheet, and an absorber mounted between the top sheet and the back sheet. A heat absorbing material is provided inside the absorber, and depressions and projections are formed on that front side of the top sheet which faces the human body.

10 Claims, 9 Drawing Sheets

(56) References Cited

U.S. PATENT DOCUMENTS

| | | | |
|---|---|---|---|
| 8,247,637 B2* | 8/2012 | Renzin et al. | 604/361 |
| 2006/0142713 A1 | 6/2006 | Long et al. | |
| 2006/0189954 A1* | 8/2006 | Kudo et al. | 604/380 |
| 2007/0049888 A1* | 3/2007 | Soerens et al. | 604/372 |
| 2007/0083172 A1 | 4/2007 | Olson | |
| 2007/0179465 A1* | 8/2007 | Sakakibara et al. | 604/385.01 |
| 2007/0298213 A1 | 12/2007 | Noda et al. | |
| 2007/0298214 A1 | 12/2007 | Noda et al. | |
| 2007/0298667 A1* | 12/2007 | Noda et al. | 442/50 |
| 2009/0287172 A1* | 11/2009 | Lowe | 604/361 |
| 2011/0178487 A1* | 7/2011 | Noda et al. | 604/367 |

FOREIGN PATENT DOCUMENTS

| | | |
|---|---|---|
| JP | 2001190596 | 7/2001 |
| JP | 2004229766 | 8/2004 |
| JP | 2005087654 | 4/2005 |
| JP | 3922722 | 3/2007 |
| JP | 2008025085 A | 2/2008 |
| WO | 9420054 A1 | 9/1994 |
| WO | 9619172 | 6/1996 |
| WO | 0160298 A2 | 8/2001 |
| WO | 2008060209 A1 | 5/2008 |

OTHER PUBLICATIONS

Search Report issued on Dec. 4, 2012 in counterpart EP application.
Office Action issued Feb. 15, 2013 in the corresponding Chilean Patent Application No. 1297-2009.
Office Action corresponding to JP2010-514461, dated Sep. 11, 2012.
Office Action corresponding to EG2010111994, dated Sep. 10, 2012.
Office Action issued Jul. 16, 2013 corresponds to Chinese Patent Application No. 200980119257.6.

* cited by examiner

<CROSS SECTIONAL VIEW>

<LONGITUDINAL SECTIONAL VIEW>

US 8,802,917 B2

ABSORBENT ARTICLE AND SANITARY NAPKIN

RELATED APPLICATIONS

The present application is a national phase of PCT/JP2009/059516, filed May 25, 2009 based on, and claims priority from, Japanese Application Number 2008-140055, filed May 28, 2008.

BACKGROUND OF THE INVENTION

1. Field of the Invention

The present invention relates to an absorbent article and a sanitary napkin each including a liquid permeable top sheet, a liquid impermeable back sheet, and an absorber interposed between the top sheet and the back sheet.

2. Description of the Related Art

Conventionally, in order to absorb body fluid such as menstrual blood excreted from a wearer, absorbent articles such as sanitary napkins have been widely used (for example, see Patent document 1). Generally, such an absorbent article has a liquid permeable top sheet, a liquid impermeable back sheet, and an absorber interposed between the top sheet and the back sheet.

CITATION LIST

Patent Literature

Patent document 1: Japanese Patent Application Publication No. 2001-190596
Patent document 2: Japanese Patent No. 3922722

SUMMARY OF THE INVENTION

Body fluid such as menstrual blood excreted from a wearer begins transpiring immediately after excretion to an absorbent article. For this reason, temperature and humidity in a space between a skin surface of the wearer and the absorbent article rise, thereby leading to a problem that the wearer feels stuffiness.

Here, Japanese Patent No. 3922722 has disclosed an absorbent article including an endothermic material which causes endothermic reaction with an attachment of a body fluid. In principle, such absorbent article can suppress increases in temperature and humidity when the wearer excretes the body fluid such as menstrual blood. The absorbent article, however, is intended as a toilet training diaper for children, and is for causing a wearer to recognize excretion of body fluid in a way that the absorbent article forcefully turns back body fluid having a temperature lowered by the endothermic material and thereby attaches the body fluid to a skin surface of the wearer. Therefore, the absorbent article is not intended to suppress the stuffiness when the body fluid such as menstrual blood is excreted.

Moreover, since the body fluid having a temperature lowered by the endothermic material is forcefully turned back and attached to the skin surface, the absorbent article gives uncomfortable feelings such as chilliness to the wearer when used as a sanitary napkin, for example.

Thus, the present invention has been made in consideration of the above-mentioned problems. An object of the present invention is to provide an absorbent article and a sanitary napkin capable of suppressing stuffiness that a wearer feels when a body fluid such as menstrual blood is excreted, and capable of reducing backflow of the body fluid having a temperature lowered.

A first aspect of the present invention is summarized by an absorbent article including a liquid permeable top sheet, a liquid impermeable back sheet, and an absorber interposed between the top sheet and the back sheet, wherein an endothermic material is disposed inside the absorber, and a depression and a projection are formed on a surface of the top sheet facing a human body.

In the first aspect, a basis weight in the projection may be larger than a basis weight in the depression.

In the first aspect, an intermediate sheet of a nonwoven fabric may be interposed between the top sheet and the absorber.

In the first aspect, in the intermediate sheet, a first density region and a second density region are formed to spread out in a planar direction, and a fiber density of the second density region may be lower than a fiber density of the first density region.

In the first aspect, the endothermic material may be disposed inside the absorber on a side facing the back sheet.

A second aspect of the present invention is summarized by a sanitary napkin including a liquid permeable top sheet, a liquid impermeable back sheet, and an absorber interposed between the top sheet and the back sheet, wherein an endothermic material is disposed inside the absorber, and a depression and a projection are formed on a surface of the top sheet facing a human body.

In the second aspect, the sanitary napkin further includes a wing extending in a width direction. In the sanitary napkin, a front region, a central region, and a rear region are provided continuously in a longitudinal direction of the absorber, the endothermic material is disposed inside the absorber in an arrangement region including at least the central region of the sanitary napkin, and a region in a longitudinal direction of the central region may be a region in a longitudinal direction of the wing.

In the second aspect, in the sanitary napkin, an embossed groove may be formed in both side portions in a width direction of the absorber, the embossed groove is formed along a longitudinal direction of the sanitary napkin, and the endothermic material may be interposed between the embossed grooves.

As described above, according to the present invention, it is possible to provide an absorbent article and a sanitary napkin that can suppress the stuffiness that a wearer feels when the body fluid such as menstrual blood is excreted, and can reduce backflow of the body fluid having a temperature lowered.

DETAILED DESCRIPTION OF THE PREFERRED EMBODIMENTS

Absorbent Article According to First Embodiment of the Present Invention

Figure 1:
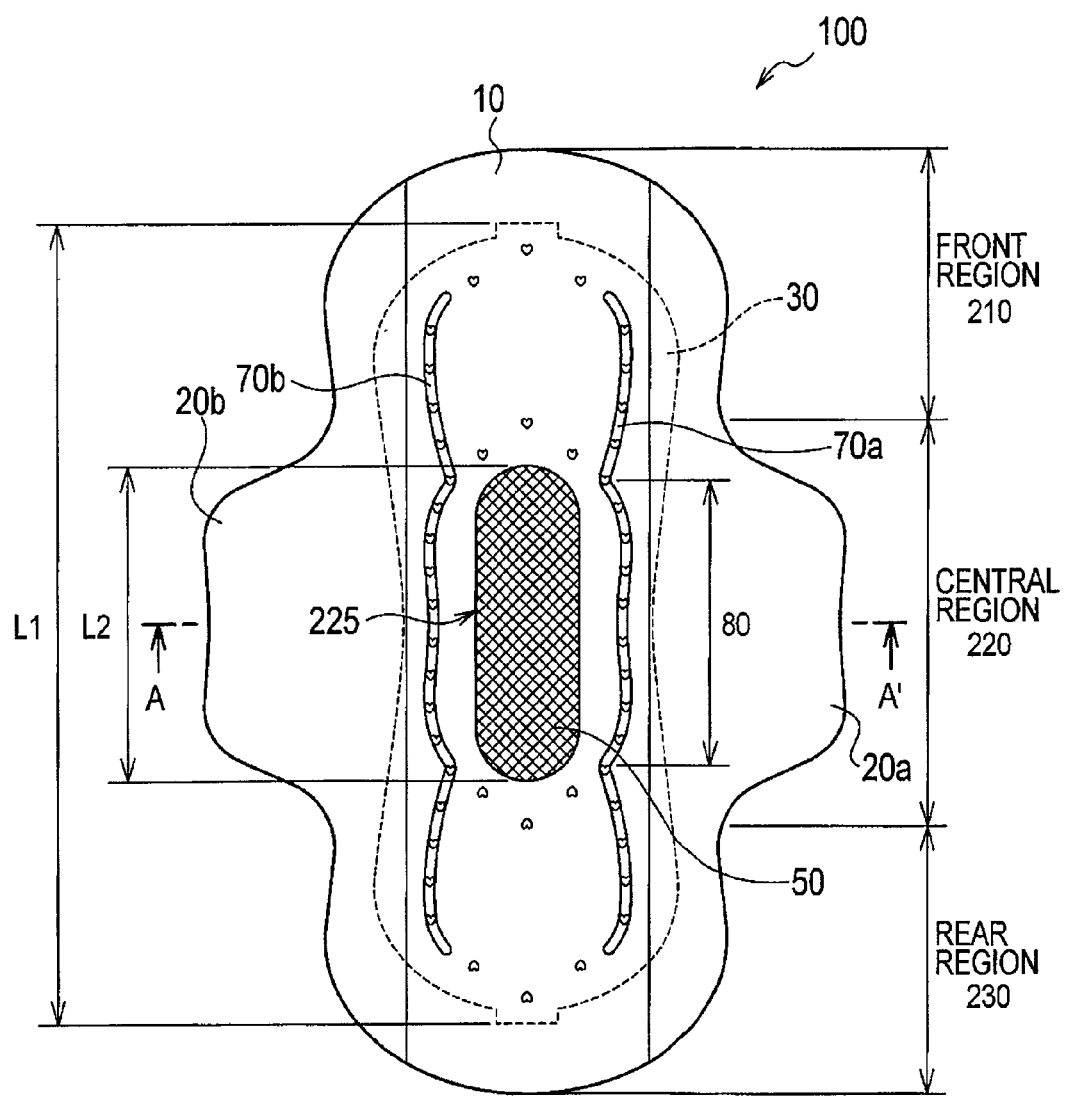
FIG. 1 is a plan view of an absorbent article according to a first embodiment of the present invention.
Figure 2:
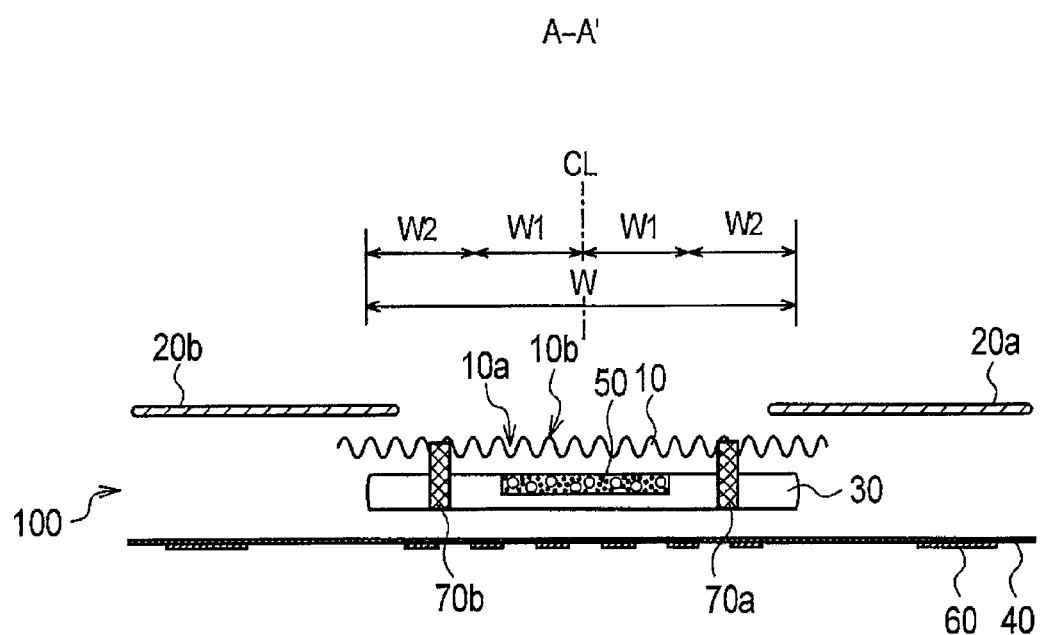
FIG. 2 is a sectional view of the absorbent article according to the first embodiment of the present invention.

With reference to FIGS. 1 to 2, a description will be given of an absorbent article according to a first embodiment of the present invention. FIG. 1 is a plan view of an absorbent article 100 according to the first embodiment of the present invention, and FIG. 2 is a sectional view of the absorbent article 100 taken along an A-A' line.

The absorbent article 100 is used as a sanitary napkin, for example. For storing in an individual packaging container and the like, the absorbent article 100 is folded inward in three or four, and is enclosed in the container. The whole shape of the absorbent article 100 may be rectangular, elliptical, gourd-shaped, etc., and is not particularly limited as long as the shape suits shapes of the wearer's body and underwear. Moreover, as an external dimension of the absorbent article 100, a dimension in a longitudinal direction is preferably in a range of "100 to 500 mm", and specifically, a range of "150 to 350 mm" is more preferable. Further, a dimension in a width direction is preferably in a range of "30 to 200 mm", and specifically, a range of "40 to 180 mm" is more preferable.

As shown in FIG. 1, in the present embodiment, the absorbent article 100 has a front region 210, a central region 220, and a rear region 230 continuously provided in a longitudinal direction (planar direction) of an absorber 30. The front region 210 is a region contacting a skin surface on a belly side of the wearer, the central region 220 is a region contacting a skin surface of a crotch part of the wearer, and the rear region 230 is a region contacting a skin surface on a buttocks side of the wearer.

Here, the central region 220 is a region to which a largest amount of a body fluid such as menstrual blood attaches when the wearer puts the absorbent article 100 on. For example, a region near the center in the width direction and in the longitudinal direction of the absorbent article 100 may be defined as the central region 220. Furthermore, when embossed grooves 70a to 70b contoured in a crotch shape (described later) are formed in the absorbent article 100 so that the absorbent article 100 can more fit the crotch part, a crotch shape portion 80 of the embossed grooves 70a to 70b (described later) may be defined as the central region 220 as shown in FIG. 1.

Moreover, in the absorbent article 100 according to the present embodiment, wings 20a to 20b extending in the width direction of the absorbent article 100 are formed so as to fix the absorbent article 100 to the underwear. When the wings 20a to 20b are thus formed, a region corresponding to the wings 20a to 20b may be defined as the central region 220. Specifically, a region in the longitudinal direction in which the wings 20a to 20b are provided may be defined as a region extending in a longitudinal direction of the central region 220. In the present embodiment, a description will be given based on an assumption that the region in the longitudinal direction in which the wings 20a to 20b are provided is the region in the longitudinal direction of the central region 220.

As shown in FIG. 2, the absorbent article 100 has a liquid permeable top sheet 10, a liquid impermeable back sheet 40, and an absorber 30 interposed between the top sheet 10 and the back sheet 40. The top sheet 10 comes in contact with the skin surface of the wearer, and the back sheet 40 comes in contact with an underwear surface. In the absorbent article 100, it is preferable that the top sheet 10, the absorber 30, and the back sheet 40 be joined in order to prevent separation between layers. Specifically, in the absorbent article 100, it is preferable that the top sheet 10 and the back sheet 40 be joined to each other in a periphery portion of the absorber 30, so that the absorber 30 is enclosed therein. As a method for joining the top sheet 10 and the back sheet 40, it is possible to employ any processing of heat embossing, ultrasonic wave, or a hot melt adhesive or a combination of these.

As shown in FIGS. 1 to 2, in the absorbent article 100, the embossed grooves 70a to 70b (the so-called hinge) are formed in the top sheet 10 and the absorber 30 in order to join the top sheet 10 and the absorber 30. The absorbent article 100 has the embossed grooves 70a to 70b formed in a pattern (embossed pattern) tracing a shape of the crotch part so as to be contoured to fit the crotch part.

As shown in FIGS. 1 to 2, the embossed grooves 70a to 70b are formed so as to extend in a longitudinal direction in both side portions in the width direction of the absorber 30. Here, in the present embodiment, when an interval in the width direction of the absorber 30 is W as shown in FIG. 2, each of the both side portions in the width direction of the absorber 30 is defined as a region shown as an interval W2 exceeding an interval W1 extending outward from the center of the absorber 30 in the width direction. For example, when the interval W1 is "10 mm", a region shown as the interval W2 exceeding "10 mm" extending outward from the center of the absorber 30 in the width direction is defined as each of the both side portions. Note that the both side portions are not limited to the content mentioned above. For example, a ratio of the interval W1 to the interval W2 is set to "1:1" or "2:1," and the both side portions each may be defined as a region of an interval W2 corresponding to this ratio. In addition, an interval in the width direction between the embossed groove 70a and the embossed groove 70b is preferably "20 to 60 mm".

Moreover, in the absorbent article 100, in order to prevent side leakage of the body fluid such as menstrual blood, gathers (not shown) including an elastic material such as a resilient material may be provided in the both side portions in the width direction of the absorber 30.

In the top sheet 10 according to the present embodiment, depressions and projections are formed on a surface of the top sheet 10 facing the human body. Specifically, as shown in FIG. 2, depressions 10a and projections 10b are formed in the top sheet 10. The surface of the top sheet 10 facing the human body means a surface opposite to a surface facing the back sheet 40 in a thickness direction of the top sheet 10.

The depressions 10a of the top sheet 10 are portions formed so as to be depressed toward the back sheet 40 in a thickness direction of the absorbent article 100. Moreover, the projections 10b of the top sheet 10 are portions formed projected rearward from the back sheet 40 in the thickness direction of the absorbent article 100.

The top sheet 10 employs a nonwoven fabric as a base material. Note that the base material for the top sheet 10 is not particularly limited to a specific one, but any material can be used as long as the material is a sheet-like material having a liquid permeable structure and the depressions 10a and the projections 10b can be formed therein such as a woven fabric or a perforated plastic sheet.

Both natural fibers and chemical fibers can be used as a material for the woven fabrics or nonwoven fabrics. Examples of the natural fibers include cellulose such as crushed pulp and cotton. Examples of the chemical fibers include regenerated cellulose such as rayon and fibril rayon, semisynthetic cellulose such as acetate and triacetate, thermoplastic hydrophobic chemical fibers, and thermoplastic hydrophobic chemical fibers subjected to hydrophilization treatment. Examples of the thermoplastic hydrophobic chemical fibers include single fibers such as polyethylene (PE), polypropylene (PP), and polyethylene terephthalate (PET), fibers obtained by graft polymerization of polyethylene and polypropylene, and composite fibers of a sheath-core structure and the like.

In particular, as the method of web forming of nonwoven fabrics, any one of dry methods (the carding method, the spun bonding method, the melt-blowing method, the air-laid method, etc.) and wet methods or a combination of the above-mentioned methods may be used. Moreover, the method of bonding may be thermal bonding, needle punching, and chemical bonding, but is not particularly limited to these methods. Alternatively, spunlace formed in a sheet form by the hydroentangling method may be used as a nonwoven fabric.

Methods for forming the depressions 10a and the projections 10b in a nonwoven fabric include, for example, a method of embossing the depressions 10a and the projections 10b on the nonwoven fabric, etc. Specifically, the depressions 10a and the projections 10b can be formed by pressing an embossing roll on the nonwoven fabric. An alternative method includes combining a roll having multiple dot-shaped projections 10b and a flat roll, combining a roll having multiple dot-shaped projections 10b and a roll having grooves, etc., and is not limited in particular.

Here, a height of the projections 10b (from a bottom surface of the depression to a top surface of the projection) is 0.3 to 15 mm, and specifically, preferably in a height of 0.5 to 5 mm. A pitch between adjacent projections 10b is 0.5 to 30 mm, and specifically, is 1 to 10 mm. The depressions 10a and the projections 10b may be continuously formed in the longitudinal direction of the absorbent article 100, or may be intermittently formed as in a zigzag pattern, etc.

The back sheet 40 has an adhesive part 60 adhering to the underwear of the wearer for preventing displacement disposed on a surface on the underwear side. A peeling sheet (not shown) is disposed by adhesion on an external surface of the adhesive part 60. A material which can be employed for the back sheet 40 includes, films mainly formed of polyethylene, polypropylene and the like, air permeable resin films, a combination of air permeable resin films joined to a nonwoven fabric such as spun bond, and spunlace and the like, plural layers of SMS, and others. Taking account flexibility of a level which does not reduce the fittingness, it is preferable that the back sheet 40 employ a film mainly formed of a low density polyethylene (LDPE) resin and having a basis weight within "15 to 30 g/m$^2$", for example.

The absorber 30 may be a product formed of a hydrophilic fiber or a polymer covered with a coating material, or may be an air-laid sheet formed into a sheet form by an air laid method.

Examples of the hydrophilic fibers include cellulose such as crushed pulp and cotton, regenerated cellulose such as rayon and fibril rayon, semisynthetic cellulose such as acetate and triacetate, granular polymers, fibrous polymers, thermoplastic hydrophobic chemical fibers, and thermoplastic hydrophobic chemical fibers subjected to hydrophilization treatment. These can be used alone or being combined. Out of these, in consideration of lower costs and workability of forming the absorber, it is preferable that crushed pulp be used.

As an example of the polymers, granular polymers such as sodium acrylate copolymer having absorbency and hygroscopicity are generally used. Alternatively, in order to obtain other properties, a granular deodorant material such as silver, copper, zinc, silica, activated carbon, aluminosilicate compounds, and zeolite may be used.

For the coating material, for example, a woven fabric, a nonwoven fabric, or the like of any type without particular limitation is usable as long as the fabric is liquid permeable and has barrier properties sufficient to prohibit a high polymer absorbent and an endothermic material (described later) from passing through the fabric. Both natural fibers and chemical fibers are usable as a material for the woven fabric and the nonwoven fabric. Examples of the natural fibers include cellulose such as crushed pulp and cotton. Examples of the chemical fibers include regenerated cellulose such as rayon and fibril rayon, semisynthetic cellulose such as acetate and triacetate, thermoplastic hydrophobic chemical fibers, and thermoplastic hydrophobic chemical fibers subjected to hydrophilization treatment.

Moreover, in consideration of lower cost and higher barrier properties, it is preferable to use as the nonwoven fabric a tissue mainly composed of crushed pulp and formed by the wet method.

When an air-laid sheet is used as the absorber 30, it is preferable that the thickness be 0.3 to 5.0 mm. Examples of the air-laid sheet include an air-laid sheet formed of fibers and a granular polymer in a sheet form by use of a binder and the like. In the air-laid sheet, the granular polymer may be distributed as a layer, or may be concentrated in a thickness direction.

Moreover, embossing may be formed in the absorber 30 in order to prevent deformation and twist during wearing, or in order to adjust a thickness. The absorber 30 can be embossed by passing between a patterned embossing roll and a flat roll. While either a lattice pattern, a dot pattern, and a wave pattern is employed as a pattern of the embossing roll, a lattice pattern is preferable because of its thickness adjustability.

A dimension in the longitudinal direction of the absorber 30 is preferably in a range of "90 to 490 mm", and specifically, it is more preferable in a range of "140 to 340 mm". Moreover, a dimension in the width direction is preferably in a range of "25 to 100 mm", and specifically, it is more preferable in a range of "35 to 80 mm".

As shown in FIG. 2, an endothermic material 50 is disposed in the absorber 30. When coming into contact with fluids such as body fluids, the endothermic material 50 is water-soluble and causes endothermic reaction to absorb surrounding heat energy. Examples of the endothermic material 50 include water-soluble materials that cause the endothermic reaction by hydration, such as potassium chloride, sodium chloride, sodium acetate, potassium nitrate, urea, sodium bicarbonate, xylitol, and trehalose. Out of these, from a viewpoint of irritativeness to the skin at the time of dissolution and stability such as long term storage, potassium chloride is preferable.
(Arrangement Area of Endothermic Material)

A description will be given of an arrangement region of the endothermic material 50 in the absorbent article 100 according to the present embodiment. For an efficient generation of the endothermic reaction with excreted menstrual blood, it is preferable that an arrangement region 225 of the endothermic material 50 include at least a region contacting the crotch part of the wearer.

In the present embodiment, the endothermic material 50 is disposed in an arrangement region including at least a central region 220 in the longitudinal direction (planar direction) of the absorbent article 100, and is disposed inside the absorber 30 in the thickness direction of the absorbent article 100. A region extending in a longitudinal direction of the central region 220 corresponds to a region in the longitudinal direction of the wings 20a to 20b. Moreover, the endothermic material 50 is disposed in a region between the embossed groove 70a and the embossed groove 70b in the width direction (planar direction) of the absorbent article 100.

In the example of FIG. 1, the arrangement region 225 in the planar direction of the endothermic material 50 is indicated by a mesh pattern. Here, as shown in FIG. 1, the arrangement region including at least the central region 220 may be a region within the central region 220, or may be an region including a part of the central region 220 and an region outside of the central region 220. As shown in FIG. 1, when a length in the longitudinal direction of the absorber 30 is defined as "L1", it is preferable that a length in the longitudinal direction of the arrangement region 225 be a length "L2" having a 30 to 50% length of "L1".

Here, assume if the length in the longitudinal direction of the arrangement region 225 is less than 30% of the length in longitudinal direction of the absorbent article 100. In that case, when an amount of menstrual blood is less, or when the wearer does not wear the absorbent article 100 on an appropriate position, the endothermic material 50 may have difficulty in causing the endothermic reaction.

On the other hand, when the length in the longitudinal direction of the arrangement region 225 is not less than 50%, the endothermic material 50 may cause the endothermic reaction with sweat or the like excreted from the crotch part of the wearer other than menstrual blood. Accordingly, chilliness may be given to the wearer more than needed.

Therefore, it is preferable that the length in the longitudinal direction of the arrangement region 225 be 30 to 50% of the length in the longitudinal direction of the absorbent article 100.

More preferably, the arrangement region 225 of the endothermic material 50 includes not only the central region 220 but also the center in the longitudinal direction of the absorbent article 100. The center of the absorbent article 100 may be the center of the entire absorbent article 100, or may be a point on the center line that divides the wings 20a and 20b equally in the longitudinal direction. When the both side portions of the absorber 30 are formed to be curved in a form projected inward in the width direction, the center in the longitudinal direction of the absorbent article 100 may be a narrowest portion in the width of the absorber 30.

Moreover, when a middle higher part projecting in the thickness direction is formed in the absorbent article 100, the center of the absorbent article 100 may be the center in a planar direction of the middle higher part. The middle higher part may be formed by laminating multiple absorbers 30 having different sizes, or may be formed so as to have its basis weight of the absorber 30 larger than basis weight in other regions.

Moreover, a density of the endothermic material 50 in the planar direction of the arrangement region 225 may be uniform on the entire surface of the absorber 30, or may be formed so as to be high in the central region 220.

It is preferable that as for a position in the thickness direction, the endothermic material 50 is disposed in a position where uncomfortable feelings to the wearer such as chilliness by the endothermic reaction of the endothermic material 50 can be avoided. The endothermic material 50 may be disposed, for example, between the top sheet 10 and the absorber 30 or inside the top sheet. However, it is preferable that the endothermic material 50 be placed inside the absorber 30 in order not to repeat the endothermic reactions in a long period of time or not to give chilliness.

Moreover, the endothermic material 50 may be disposed at a uniform density in the thickness direction of the absorber 30. In order to reduce temperature even with a little amount of the excreted body fluid such as menstrual blood, it is preferable that the endothermic material 50 be disposed in a position on the skin surface side in the thickness direction of the absorber 30.

(Grain Diameter of Endothermic Material)

A description will be given of a grain diameter of the endothermic material 50 according to the present embodiment. Endothermic materials having different grain diameters are disposed in the endothermic material 50 according to the present embodiment. Specifically, the endothermic material 50 includes endothermic materials having a grain diameter in a range of 150 μm to 850 μm and having different grain diameters. The grain diameter of the endothermic material is not particularly limited, but may be within a range of 300 to 800 μm or within a range of 350 to 600 μm from a viewpoint of feeling of foreign objects and a viewpoint of productivity.

Here, when components of the endothermic materials are the same, the endothermic material having a larger grain diameter takes more time until completely dissolves. This is because the endothermic material begins to dissolve from an uppermost surface of the grains when dissolving by hydration, and therefore, the grain having larger diameter, that is, having larger volume takes more time to completely dissolve.

In order to cause the endothermic reaction even in the case of long-time excretion or repeated excretion, a larger grain diameter is more preferable. However, if the absorber 30 includes only an endothermic material having a larger grain diameter, rigidity of the absorber 30 increases, and therefore, feeling of foreign objects is given to the wearer.

Accordingly, in order to cause the endothermic material 50 to cause the endothermic reaction for a long time and to prevent an excessive increase in the rigidity of the absorber 30, it is preferable that endothermic materials having different grain diameters be included.

(Configuration of Endothermic Material in Absorber)

A description will be given of a configuration of the endothermic material 50 according to the present embodiment. As for the endothermic material 50, a sheet covering only the endothermic material 50 with a coating material may be disposed on an upper surface of the absorber 30, or the endothermic material 50 may be disposed as a layer between pulps. Further, the endothermic material 50 may be sandwiched between the top sheet 10 and the absorber 30.

Here, since the endothermic material 50 is water-soluble, for example, when a region of the endothermic material 50 where a diameter of a grain is small dissolves at a first excretion of menstrual blood, a space is generated in the endothermic material 50. In this case, when the menstrual blood is repeatedly excreted, it becomes difficult for the menstrual blood to move from the top sheet 10 to the back sheet 40. As a result, the menstrual blood stagnates in the top sheet 10, and thus the wearer may feels uncomfortable.

As mentioned above, it is preferable that the endothermic material 50 be blended with pulp and the like, and be dispersed to some extent. Specifically, the absorber 30 is preferably obtained by mixing pulp in a rage of 60 to 98%, the granular endothermic material 50 in a range of 40 to 2%, and a granular polymer in a range of 20 to 0%, the mixture is then covered with a tissue, and subsequently the mixture is formed into a sheet having a basis weight of 100 to 2,000 g/m² and a height of 1 to 50 mm by embossing. Embossing is performed for preventing deformation of the absorber, and an embossed area rate is preferably in a range of 10 to 100%, and specifically, in a range of 30 to 80%.

It is preferable that the endothermic material 50 in the absorber 30 has a configuration which allows the endothermic material 50 to repeat the endothermic reactions by the body fluid such as menstrual blood in a long period of time, or a configuration that gives no chilliness. Specifically, for an upper layer material (top sheet 10 side), pulp of 50 to 150 gsm and potassium chloride of 0.5 to 3.0 g are blended. For a lower layer material (back sheet 40 side), pulp of 50 to 200 gsm and a high polymer absorbent of 0.1 to 0.5 g are blended. Then, the upper layer material and the lower layer material are layered, covered with a tissue, and subsequently, embossed. This may be used as the endothermic material 50.

(Mixing Amount of Endothermic Material)

A description will be given of a mixing amount of the endothermic material 50 in the absorber 30 according to the present embodiment. The mixing amount of the endothermic material 50 is influenced by the variety of heat of dissolution and solubility, which depend on a kind of the endothermic material 50, and also by an arrangement position of the endothermic material 50. Here, in consideration of suppressing sharp increases in temperature and humidity in the space between the skin surface and the absorbent article 100 and of giving no uncomfortable feelings to the wearer such as chilliness, a weight of the endothermic material 50 per sheet in the absorbent article 100 is preferably in a range of 0.1 to 10 g, and more specifically, in a range of 0.5 to 5 g.

As an example, a description will be given of a case where a sanitary napkin is used as the absorbent article 100 and potassium chloride is used as the endothermic material 50.

It is known that an average absorbed amount per a napkin in a day (the first to third day) during a menstrual period when much menstrual blood is excreted is generally approximately 6.0 ml. It is also known that solubility of potassium chloride is approximately 27.0% in an experiment liquid (physiological saline) adjusted to 37° C.±5° C.

From these, potassium chloride that can dissolve to 6.0 ml of menstrual blood is approximately 2.0 g, and even when not less than potassium chloride 2.0 g is mixed, the excessive potassium chloride does not cause the endothermic reaction. Accordingly, when potassium chloride is used in sanitary napkins for days with much menstrual blood loss, a mixing amount of potassium chloride is preferably in a range of 0.5 to 3.0 g, and more preferably in a range 1.0 to 2.0 g.

According to the absorbent article 100 of the first embodiment of the present invention, the endothermic material 50 is disposed inside the absorber 30. Accordingly, when the body fluid such as menstrual blood is excreted, the absorbent article 100 prevents the increases in temperature and humidity of the absorber 30 by the endothermic reaction of the endothermic material 50. In other words, the absorbent article 100 can suppress the stuffiness that the wearer feels when the body fluid such as menstrual blood and urine is excreted.

Further, when the water-soluble material used as the endothermic material 50 is dissolved into the blood, the solute concentration in the blood plasma increases. Therefore, the osmotic pressure of the blood plasma increases, and the water included in the red blood cell is discharged. This results in contraction of the red blood cell. Thus, the volume of the red blood cell decreases. When the volume of the red blood cell is decreased in this manner, surface tension of the blood increases, thereby contact angle of the blood with respect to the top sheet 10 increases. In other words, leakage probability of the red blood cell decreases.

As described above, when the water-soluble material is dissolved into the blood that has once passed through the top sheet 10, the leakage probability of the blood decreases. Therefore, the blood is not easily returned to the skin surface through the top sheet 10. Thus, the wearer can feel sense of dryness.

Moreover, according to the absorbent article 100 of the first embodiment of the present invention, the depressions 10a and the projections 10b are formed in the top sheet 10. Therefore, even when pressure from the wearer being in contact with the skin surface of the wearer is applied to the projections 10b of the top sheet 10, the depressions 10a can accommodate the body fluid leaked from the projections 10b. Therefore, backflow of the body fluid to the wearer can be reduced.

Further, according to the absorbent article 100 of the first embodiment of the present invention, the depressions 10a and the projections 10b are formed in the top sheet 10. For this reason, compared with a case where the depressions 10a and the projections 10b are not formed, an area of the top sheet 10 contacting the skin surface can be reduced. Therefore, it is possible to suppress the stuffiness that the wearer feels when the wearer comes in contact with the top sheet 10 to which the body fluid attaches.

In this way, according to the absorbent article 100 of the first embodiment of the present invention, it is possible to suppress the stuffiness that the wearer feels when the body fluid such as menstrual blood is excreted, and to reduce backflow of the body fluid having a temperature lowered.

Moreover, according to absorbent article 100 of the first embodiment of the present invention, the endothermic material 50 is disposed in the region including at least the central region 220 of the absorbent article 100. Additionally, in the present embodiment, the central region 220 corresponds to the region of the wings 20a to 20b in the longitudinal direction.

Here, the absorbent article 100 is generally used so that a region between the wing 20a and wing 20b may come in contact with the crotch part when the absorbent article 100 is put on. Accordingly, by defining the region of the wings 20a to 20b in the longitudinal direction as the central region 220 and disposing the endothermic material 50 in the region including at least the central region 220, the body fluid from the wearer such as menstrual blood can be made to attach to the endothermic material 50 more securely so as to cause the endothermic reaction.

Moreover, in the absorbent article 100 according to the first embodiment of the present invention, the embossed grooves 70a to 70b are formed in order to join the top sheet 10 and the absorber 30. The endothermic material 50 is disposed in the region between the embossed groove 70a and the embossed groove 70b.

Accordingly, in the absorbent article 100 according to the first embodiment of the present invention, the top sheet 10 and the absorber 30 are formed so as not to easily separate from each other. For this reason, the body fluid from the wearer such as menstrual blood can be made to attach to the endothermic material 50 more securely to cause the endothermic reaction. Further, according to the absorbent article 100, the endothermic material 50 is disposed in the region between the embossed groove 70a and the embossed groove 70b. Accordingly, even when the absorbent article 100 is twisted, endothermic material 50 is less likely to come out of the absorber 30.

(Absorbent Article According to Second Embodiment of the Present Invention)

Figure 3:
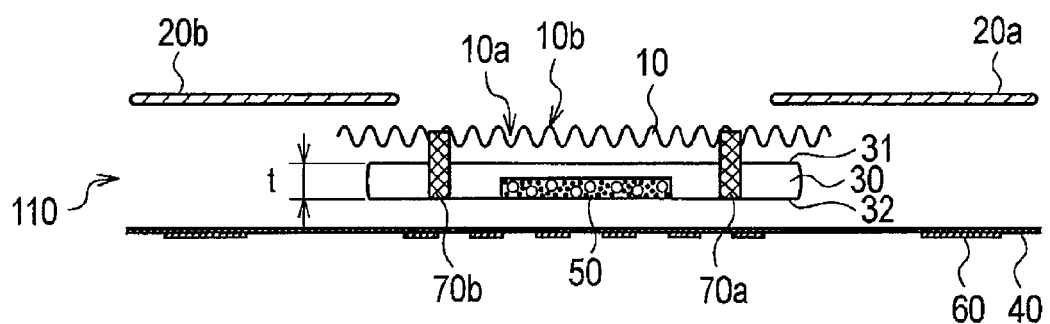
FIG. 3 is a sectional view of an absorbent article according to a second embodiment of the present invention.

With reference to FIG. 3, a description will be given of an absorbent article according to a second embodiment of the present invention. Hereinafter, the absorbent article according to the second embodiment of the present invention will be described focusing on differences from the absorbent article according to the first embodiment of the present invention.

In the absorbent article 110 according to the second embodiment of the present invention, the endothermic material 50 is disposed inside the absorber 30 on the back sheet 40 side.

Specifically, in the present embodiment, in the thickness direction of the absorber 30, a density of the endothermic material 50 on the top sheet 10 side is higher than a density of the endothermic material 50 on the back sheet 40 side. In other words, the endothermic material 50 inside the absorber 30 has different densities in the thickness direction of the absorber 30.

For example, as shown in FIG. 3, an interval in the thickness direction of the absorber 30 is defined as "t". Moreover, a half of the interval "t" is defined as "t1". In the present embodiment, in the thickness direction, the density of the endothermic material 50 inside the absorber 30 in the interval "t1" extending from a surface 32 placed on the back sheet 40 side of the absorber 30 is higher than the density of the endothermic material 50 inside the absorber 30 in the interval "t1" extending from a surface 31 placed on the top sheet 10 side of the absorber 30.

In the absorbent article 110, when an interval (the first interval) between the surface 31 on the top sheet 10 side of the absorber 30 and the endothermic material 50, and an interval (the second interval) between the surface 32 on the back sheet 40 side of the absorber 30 and the endothermic material 50 are provided in the thickness direction of the absorber 30, the interval between the surface 31 and the endothermic material 50 may be formed so as to be larger than the interval between the surface 32 and the endothermic material 50.

Further, in the absorbent article 110 according to the second embodiment of the present invention, leakage probability of the red blood cell can decrease since the water-soluble material is dissolved into the blood that has once passed through the top sheet 10. Therefore, the blood is not easily returned to the skin surface through the top sheet 10. Thus, the wearer can feel sense of dryness.

According to the absorbent article 110 of the second embodiment, the endothermic material 50 is disposed on the back sheet 40 side. Accordingly, backflow of the body fluid to the surface sheet 10 can be reduced, the body fluid having the temperature lowered by the endothermic reaction of the endothermic material 50. In other words, according to the absorbent article 110 of the second embodiment, the body fluid with lowered temperature is less likely to flow back to the wearer.

(Absorbent Article According to Third Embodiment of the Present Invention)

Figure 4:
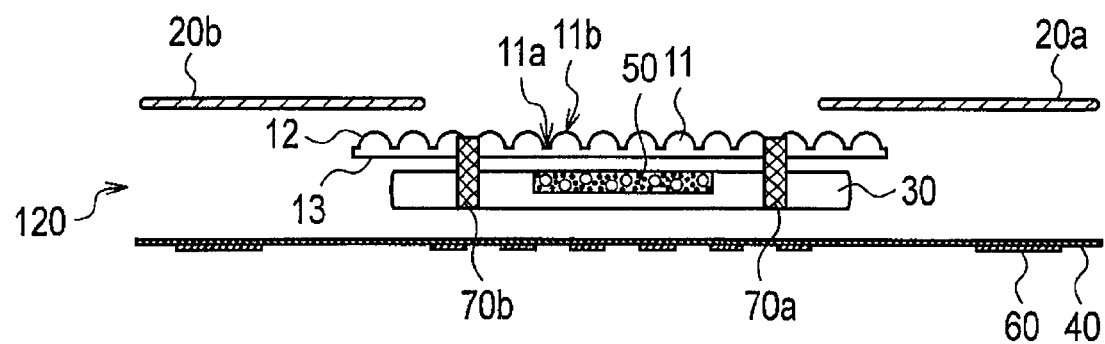
FIG. 4 is a sectional view of an absorbent article according to a third embodiment of the present invention.

With reference to FIG. 4, a description will be given of an absorbent article according to a third embodiment of the present invention. Hereinafter, the absorbent article according to the third embodiment of the present invention will be described focusing on differences from the absorbent article according to the first embodiment of the present invention. FIG. 4 is a sectional view of the absorbent article 120 according to the third embodiment of the present invention.

As shown in FIG. 4, in the absorbent article 120 according to the present embodiment, a top sheet 11 has depressions 11a and projections 11b formed on a surface of the top sheet 11 facing the human body. In addition, a basis weight in the projections 11b of the top sheet 11 is larger than a basis weight in the depressions 11a of the top sheet 11.

Specifically, the basis weight of the depressions 11a is, for example, in a range of 3 to 200 g/m², and more preferably, in a range of 5 to 80 g/m². Moreover, the basis weight of the projections 11b is larger than the basis weight of the depressions 11a, and the basis weight of the projections 11b is, for example, in a range of 15 to 250 g/m², and more preferably, in a range of 20 to 120 g/m².

Further, the depressions 11a and the projections 11b are formed so as to have approximately an equal fiber density. For example, it is preferable that the fiber density of the projections 11b be not more than 0.20 g/cm³, and the fiber density of the depressions 11a be not more than 0.18 g/cm³.

Here, the surface of the top sheet 11 facing the human body is a surface 12 on a side opposite to the back sheet 40 side in the thickness direction of the absorbent article 120, as shown in FIG. 4. As shown in FIG. 4, a surface of the top sheet 11 placed on the back sheet 40 side is a surface 13 in the thickness direction of the absorbent article 120.

Except that the depressions 11a and the projections 11b are formed on the surface 12 of the top sheet 11 facing the human body, the absorbent article 120 according to the present embodiment is formed in a same manner as in the case of the absorbent article 100 according to the first embodiment.

Moreover, the depressions 11a of the top sheet 11 are portions formed so as to be depressed toward the back sheet 40 in the thickness direction of the absorbent article 120. The projections 11b of the top sheet 11 are portions formed to be projected rearward from the back sheet 40 in the thickness direction of the absorbent article 120. Further, in the present embodiment, the depressions 11a and the projections 11b are continuously formed in the top sheet 11 in the longitudinal direction of the absorbent article 120. The depressions 11a and the projections 11b may be formed at predetermined intervals in the longitudinal direction and width direction of the top sheet 11.

Methods of forming the depressions 11a and the projections 11b include a method of forming the depressions 11a and the projections 11b at the same time as forming a nonwoven fabric. Specifically, to a web continuum that is a group of fibers, hot air is blown at predetermined intervals in a width direction (Crossing Direction) and continuously in a longitudinal direction (Machine Direction). At this time, by sucking the hot air from underneath the web, the web can be formed so as to have depressions and projections in which the basis weight of the projections 11b is larger than the basis weight of the depressions 11a. Subsequently, the web is conveyed into an oven set at a predetermined temperature and fibers are fused. In this way, the depressions 11a and projections 11b of the top sheet 11 are formed.

As an alternative method, it is also possible to use a method of forming predetermined depressions and projections by embossing used in order to fuse fibers such as spun-bonded nonwoven fabric or point-bonded nonwoven fabric. Furthermore, another method may be used. In this method, a web (upper layer web) mainly composed of fibers having low heat shrinkability and a web (lower layer web) mainly composed of fibers having high heat shrinkability are layered on each other and partially integrated by dotted embossing. Subsequently, the partially integrated web is conveyed into an oven set at a predetermined temperature, and thus the lower layer web is thermally contracted and the upper layer web partially rises. In employing either methods, desirably, the basis weight of the projections 11b is formed so as to be larger than the basis weight of the depressions 11a, and the depressions 11a and the projections 11b are formed so as to have approximately an equal fiber density.

In the absorbent article 120 according to the third embodiment of the present invention, the basis weight in the projections 11b of the top sheet 11 is larger than the basis weight in the depressions 11a of the top sheet 11. Accordingly, even when the skin surface of the wearer comes in contact with the top sheet 11 of the absorbent article 120, and external pressure applied to the top sheet 11 becomes larger, the projections 11b is less likely to be crushed and a thickness of the top sheet 11 can be maintained. For this reason, backflow of the body fluid such as menstrual blood can be reduced.

Moreover, in the absorbent article 120 according to the third embodiment of the present invention, the depressions 11a and the projections 11b are formed so as to have approximately an equal fiber density.

Here, when, for example, the depressions 11a are formed by compression processing such as embossing, the fiber density of the depressions 11a becomes significantly higher than the fiber density of the projections 11b. In other words, in the top sheet 11, a region having a higher fiber density through which the body fluid does not flow easily (depressions 11a) and a region having a lower fiber density through which the body fluid flows easily (projections 11b) are formed. In this case, the body fluid such as menstrual blood might stagnate in the region having the higher fiber density (depressions 11a) and might flow back when the skin surface of the wearer comes in contact with the top sheet 11.

In the absorbent article 120 according to the third embodiment of the present invention, the depressions 11a and the projections 11b are formed so as to have approximately an equal fiber density. In other words, the top sheet 11 is formed so as not to include the region having the higher fiber density through which the body fluid does not flow easily (depressions 11a). Accordingly, the body fluid can be less likely to stagnate and the body fluid can smoothly flow to the back sheet 40 side.

(Absorbent Article According to Fourth Embodiment of the Present Invention)

Figure 5:
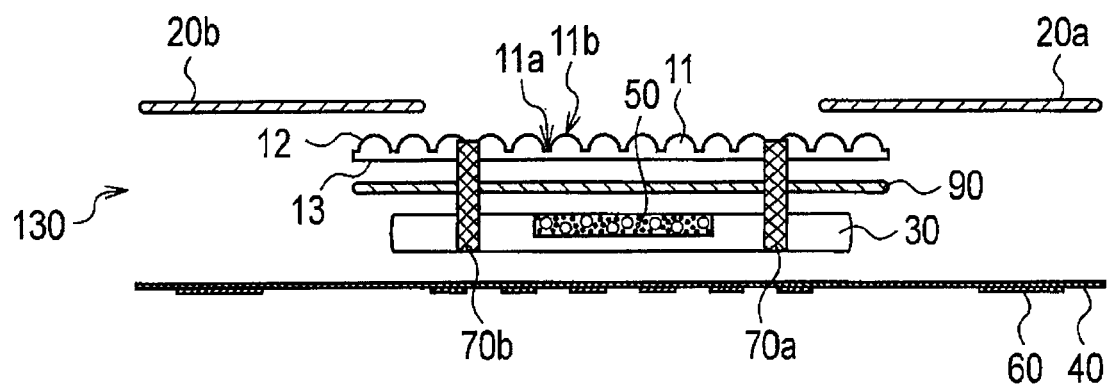
FIG. 5 is a sectional view of an absorbent article according to a fourth embodiment of the present invention.

With reference to FIG. 5, a description will be given of an absorbent article according to a fourth embodiment of the present invention. Hereinafter, focusing on differences from the absorbent article according to the third embodiment of the present invention, a description will be given of the absorbent article according to the fourth embodiment of the present invention. FIG. 5 is a sectional view of the absorbent article 130 according to the fourth embodiment of the present invention.

As shown in FIG. 5, in the absorbent article 130 according to the present embodiment, an intermediate sheet 90 that is a nonwoven fabric is interposed between the top sheet 11 and the absorber 30. Except that the intermediate sheet 90 is disposed, the absorbent article 130 according to the present embodiment has the same configuration as that of the absorbent article 120 according to the third embodiment.

In the present embodiment, an air-through nonwoven fabric (35 gsm) is used as a material of the intermediate sheet 90. In the absorbent article 130 according to the present embodiment, an area in a planar direction of the intermediate sheet 90 is formed to be approximately the same as that of the top sheet 11.

In the absorbent article 130 according to the fourth embodiment of the present invention, the intermediate sheet 90 is interposed between the top sheet 11 and the absorber 30. Accordingly, a thickness between the absorber 30 and the top sheet 11 can be increased by the nonwoven fabric. Therefore, the backflow of the body fluid from the top sheet 11 can be reduced, the body fluid having a temperature being lowered by the endothermic reaction of the endothermic material 50.

(Absorbent Article According to Fifth Embodiment of the Present Invention)

Figure 6:
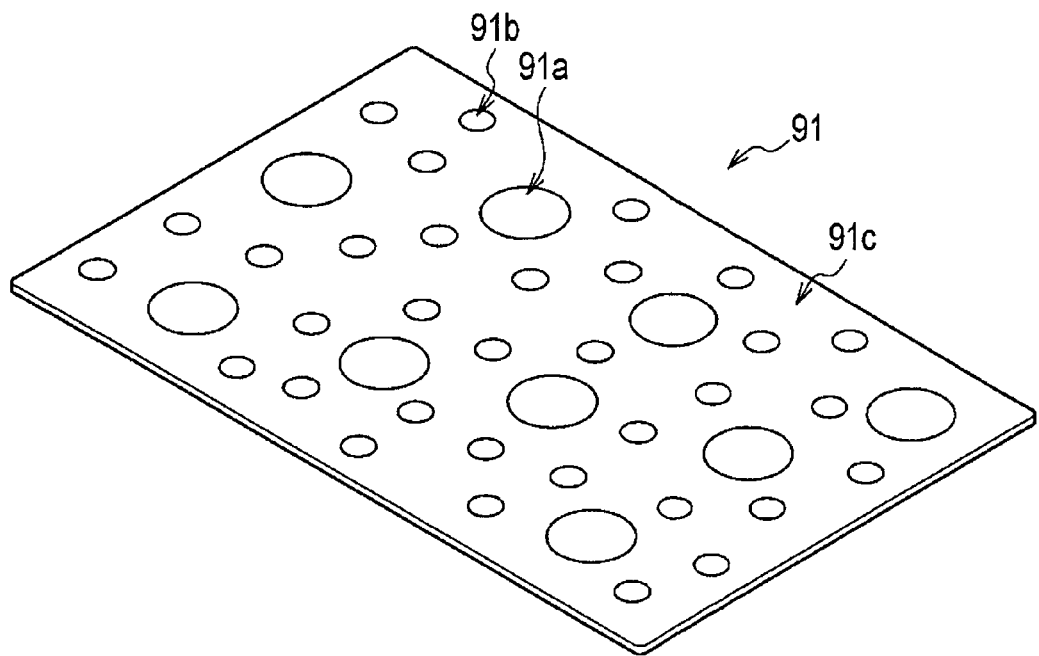
FIG. 6 is a perspective view of an intermediate sheet according to a fifth embodiment of the present invention.

With reference to FIG. 6, a description will be given of an absorbent article according to a fifth embodiment of the present invention. Hereinafter, focusing on differences from the absorbent article according to the third embodiment of the present invention, a description will be given of the absorbent article according to the fifth embodiment of the present invention. FIG. 6 is a perspective view of an intermediate sheet 91 according to the fifth embodiment of the present invention.

As shown in FIG. 6, in the absorbent article 130 according to the present embodiment, a high density region (the first density region) and a low density region (the second density region) are formed in the intermediate sheet 91 spreading in a planar direction, and a fiber density of the low density region is lower than a fiber density of the high density region.

Specifically, as shown in FIG. 6, high density regions 91a to 91b and a low density region 91c are formed in the intermediate sheet 91 according to the present embodiment. Moreover, a basis weight of the low density region 91c is lower than a basis weight of the high density regions 91a to 91b. The high density regions 91a to 91b and the low density region 91c are formed spreading in the planar direction at predetermined intervals.

In the example of FIG. 6, an area of the high density region 91a is formed larger than that of the high density region 91b. Moreover, in the example of FIG. 6, a case is taken as an example where two types of regions having different areas are formed as the high density regions 91a to 91b in the planar direction of the intermediate sheet 91. However, the area of these regions will not be limited to the two types. In the planar direction of the intermediate sheet 91, the high density regions 91a to 91b may be regularly formed at predetermined intervals, or may be irregularly formed.

Using an example, a description will be given of a method of forming the high density regions 91a to 91b and the low density region 91c in the intermediate sheet 91. For example, a web obtained by blending low heat shrinkable fibers and fibers having little heat shrinkability is conveyed into an oven set at a predetermined temperature, the low heat shrinkable fibers are thermally contracted so as to wrap around the fibers having little heat shrinkability in the circumference of the low heat shrinkable fibers. Thereby, a web having irregular depressions and projections is formed. Immediately after that, the web is passed through between flat rolls to have their projections crushed. In this way, the web is formed into an air-through nonwoven fabric having both sides approximately flat. Regions of the crushed projections are the high density regions 91a to 91b.

In the absorbent article according to the fifth embodiment of the present invention, the high density regions 91a to 91b (the first density region) and the low density region 91c (the second density region) are formed in the intermediate sheet 91 spreading in the planar direction. Accordingly, when a large amount of the body fluid such as menstrual blood are excreted to the absorbent article 130 in a short period of time, the low density region 91c can allow the body fluid to flow to the absorber 30 therethrough. Consequently, the body fluid can be prevented from stagnating in a wide range of the top sheet 11.

Moreover, the high density regions 91a to 91b can allow the body fluid that would otherwise remain on the top sheet 11 to flow from the top sheet 11 to the absorber 30, using density gradient between the high density regions 91a to 91b of the intermediate sheet 91 and the top sheet 11. This makes it hard for the body fluid to remain in the top sheet 11 or the intermediate sheet 91, and therefore a larger amount of the body fluid can be made to attach to the endothermic material 50 disposed inside the absorber 30. Therefore, in the absorbent article 130, the generation of the endothermic reaction of the endothermic material 50 can be urged and increases in the temperature and humidity can be suppressed. Accordingly, in the absorbent article 130, it is possible to suppress the stuffiness that the wearer feels when the body fluid such as menstrual blood and urine are excreted.

Menstrual blood includes a lot of solid contents such as endometrium. The endothermic material 50 hardly causes the endothermic reaction with the attachment of the solid contents. For this reason, it is preferable that the solid contents be filtered until the menstrual blood absorbed from the top sheet 11 attaches to the endothermic material 50. The high density regions 91a to 91b of the intermediate sheet 91 easily filter the solid contents of the menstrual blood into fibers. Therefore, the high density regions 91a to 91b can prevent the endothermic material 50 from deteriorating its endothermic performance.

Other Embodiments

While the sanitary napkin has been described as an example of the absorbent article in the above-mentioned embodiments, the present invention will not be limited to the sanitary napkin, and can also be applied to feminine absorbent articles such as panty liners. Further, the absorbent article can also be applied to incontinence pads and diapers.

As mentioned above, while the present invention has been described in detail using the above-mentioned embodiments, it should be obvious for those skilled in the art that the present invention should not be limited to the embodiments described herein. The present invention can be implemented as modifications and modified aspects, without departing from the spirit and scope of the present invention defined by the description of the scope of claims. Accordingly, the description herein is aimed at describing an example, and it does not have any restrictive sense to the present invention. Further, embodiments and modifications of the present invention can be combined.

EXAMPLES

Next, more detailed description will be given of the present invention using examples. However, the present invention will not be limited to the following examples at all.
<Test Device>

Figure 7A:
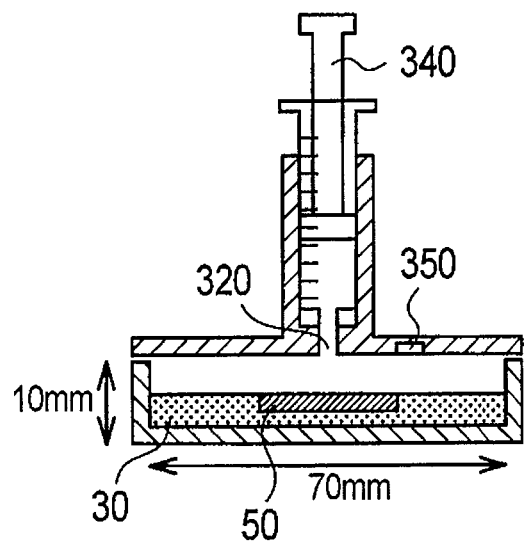
FIG. 7A is a cross sectional view of a test device according to Example 1 of the present invention.
Figure 7B:
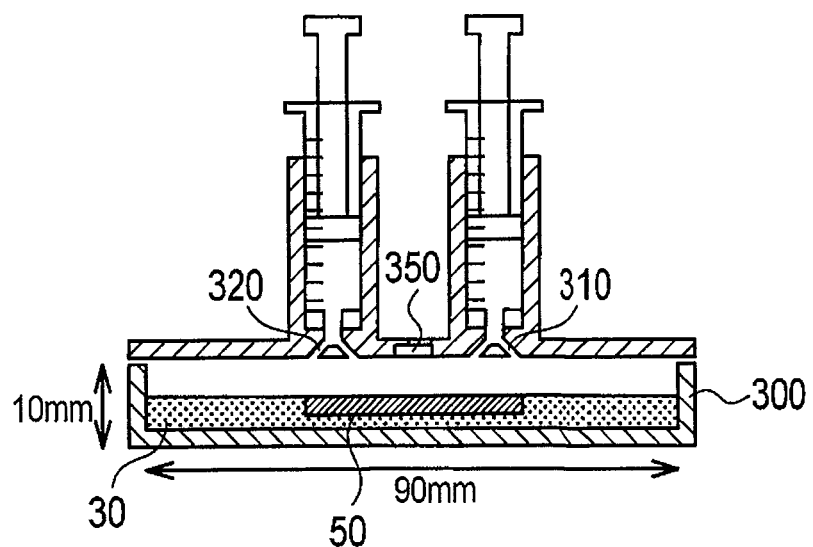
FIG. 7B is a longitudinal sectional view of the test device according to Example 1 of the present invention.

First, in order to reproduce a space between a skin and an absorbent article, and in order to reproduce a diffusion state of body fluid during wearing, a test device as shown in FIG. 7A to FIG. 7B was produced. FIG. 7A is a cross sectional view of the test device, and FIG. 7B is a longitudinal sectional view of the test device.

In the test device, an enclosed space of 90 mm long, 70 mm wide, and 10 mm deep was produced with an acrylic container 300. In order to measure changes in temperature and humidity of the enclosed space, a temperature and humidity sensor 350 was installed in the test device.

In order to diffuse a test liquid in the vertical direction, an acrylic lid was installed above the acrylic container 300, the lid provided with holes into which two syringes 340 could be inserted in a vertical direction, and holes 310 to 320 through which drops of the test liquid passed in the vertical direction to drop at two locations respectively from the syringes 340. In other words, the test liquid could be dropped from four holes aligned in the vertical direction.

In order to match with salt concentration of a body fluid, physiological saline was used as a test liquid having a composition in which distilled water is mixed with sodium chloride in a way that sodium chloride concentration might be 0.9%.

A temperature of the test liquid was adjusted to 37° C.±5° C., in order to match with a temperature of the body fluid.

Example 1

Sample 1 having an absorber in which an endothermic material was disposed was produced. Specifically, first, as an upper layer material of the absorber, pulp of 150 gsm and potassium chloride of 1.5 g were blended, and the mixture was formed to have a longitudinal dimension of 100 mm and a width dimension of 30 mm.

An average grain diameter of potassium chloride (endothermic material) was 425 μm, and potassium chloride in a range of 325 to 525 μm was 42% of an entire volume.

Moreover, as a lower layer material of the absorber, pulp of 130 gsm and a high polymer absorbent 0.3 g were blended, and the mixture was formed to have a longitudinal dimension of 200 mm and a width dimension of 70 mm.

The upper layer material and the lower layer material thus formed were layered and covered with a tissue of 14 gsm. After covering, a thickness of the absorber was adjusted to 3.4 mm by embossing.

After embossing, 35 gsm of an air-through nonwoven fabric as a top sheet was placed on the absorber. In order to integrate the top sheet and the absorber, both sides thereof were joined by embossing.

After joining the top sheet and the absorber by embossing, in order to dispose the top sheet and the absorber on the test device, the top sheet and the absorber were cut into a longitudinal dimension of 90 mm and a width of 70 mm. The obtained product was formed as Sample 1.

As Sample 2, an absorber in which no endothermic material was disposed was produced. Sample 2 was produced in the same method as that of Sample 1 except that potassium chloride (endothermic material) was not disposed in the upper layer material of the absorber.
(Evaluation Method 1)

An evaluation test was conducted in the following manner using Sample 1 thus produced. The evaluation test was conducted under an environment of 35° C.±5° C. and 75 RH %±5 RH %.

First, the acrylic lid of the test device was opened, and Sample 1 was installed in the acrylic container 300. Next, the acrylic lid was closed and Sample 1 was left in the container for 15 minutes for stabilization. At the time when the acrylic lid was closed, measurements of the temperature and humidity of the enclosed space were begun.

After 15 minutes from the start of the measurements (after stabilization), 2 ml of the test liquid adjusted to 37° C.±5° C. was dropped. After 30 minutes from that, 2 ml of the test liquid at the same temperature was dropped. This process was repeated 5 times and a total of 10 ml of the test liquid was dropped. From the start of the measurements, the temperature and humidity for 2 hours and 45 minutes in total were measured.

Moreover, the above-mentioned evaluation test was similarly conducted on Sample 2 as well.

(Evaluation Result 1)

Figure 8A:
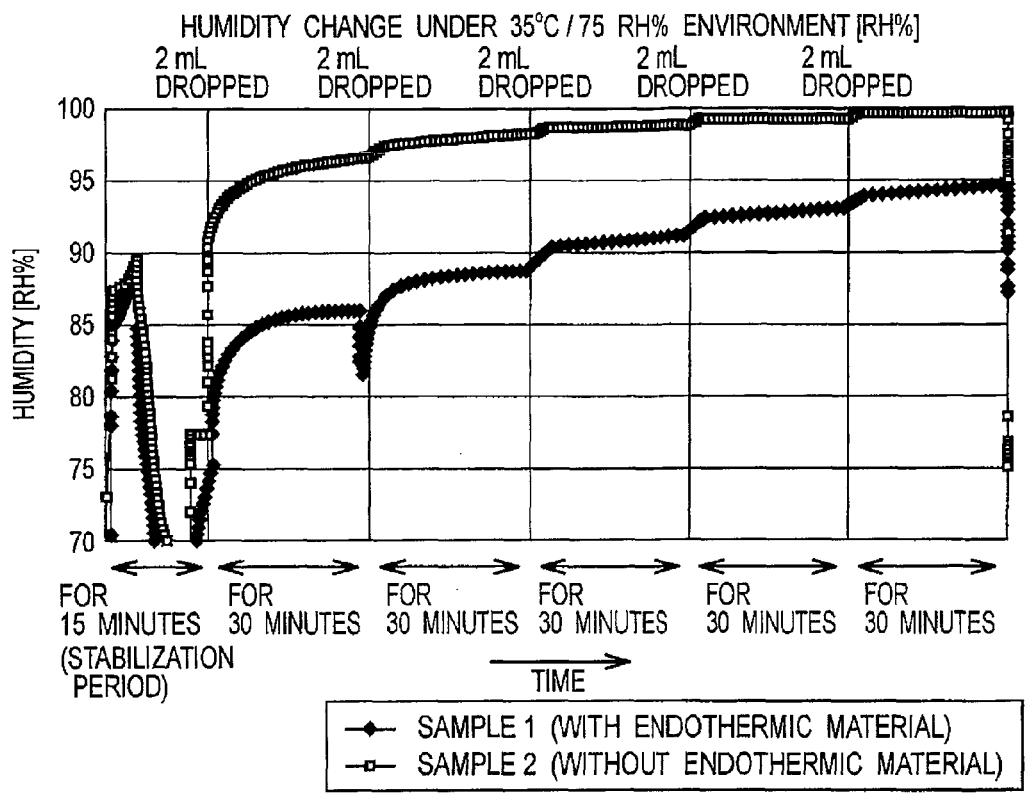
FIG. 8A is a graph that shows changes in humidity according to Example 1 of the present invention.
Figure 8B:
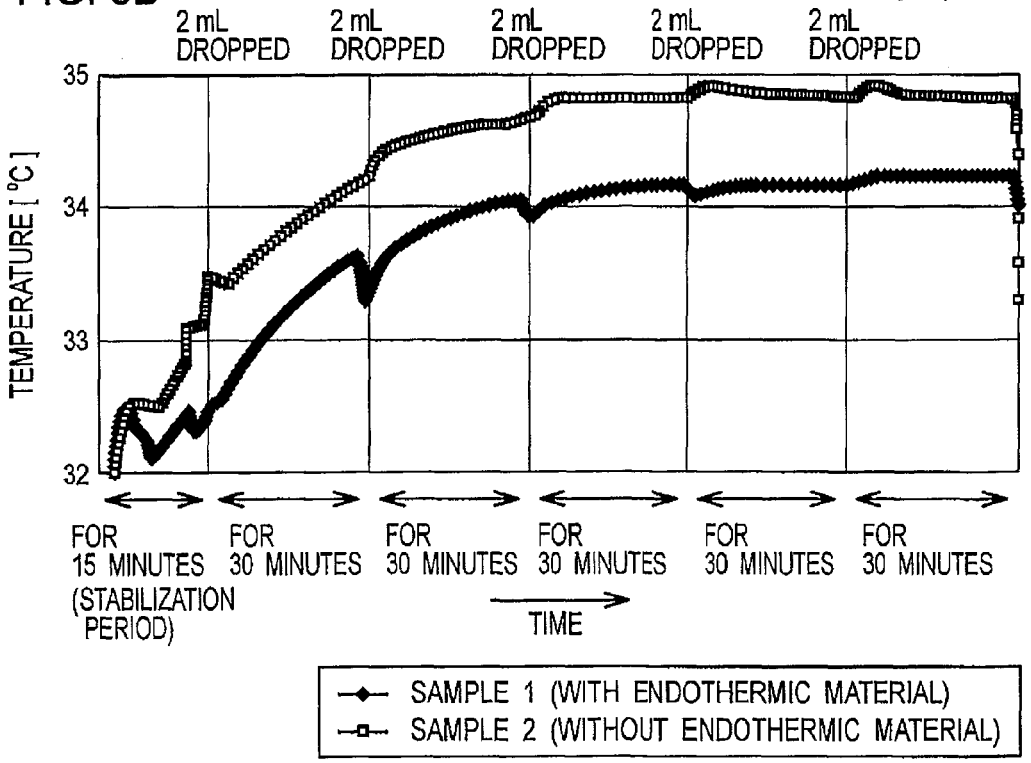
FIG. 8B is a graph that shows changes in temperature according to Example 1 of the present invention.

FIGS. 8A to 8B show measurement results of the temperature and humidity obtained by the above-mentioned evaluation test. FIG. 8A shows the measurement results of humidity, and FIG. 8B shows the measurement results of temperature.

As shown in FIGS. 8A to 8B, in Sample 2, the temperature and humidity in the enclosed space of the test device sharply rose immediately after dropping 2 ml of the test liquid. In contrast, the temperature and humidity in Sample 1 rose less than those in Sample 2. Moreover, even when 2 ml of the test liquid was repeatedly (5 times) dropped, the temperature and humidity in Sample 1 rose less than those in Sample 2.

(Evaluation Method 2)

The following evaluation test was conducted using obtained Sample 1. The evaluation test was conducted under an environment of 35° C.±5° C. and 75 RH %±5 RH %.

First, the acrylic lid of the test device was opened, and Sample 1 was installed in the acrylic container 300. Next, the acrylic lid was closed and Sample 1 was left in the container for 15 minutes for stabilization. At the time when the acrylic lid was closed, measurements of the temperature and humidity of the enclosed space were begun.

After 15 minutes from the start of the measurements (after stabilization), 6 ml of the test liquid adjusted to 37° C.±5° C. was dropped. Subsequently, the temperature and humidity for 60 minutes were measured.

Moreover, the above-mentioned evaluation test was similarly conducted on Sample 2 as well.

(Evaluation Result 2)

Figure 9A:
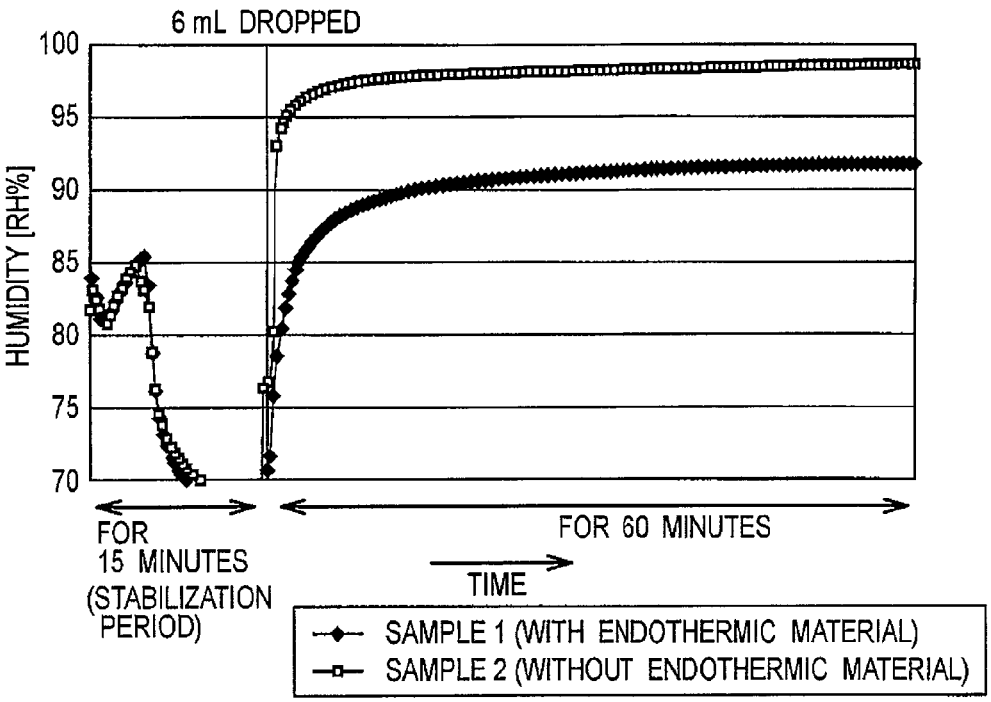
FIG. 9A is a graph that shows changes in humidity according to Example 1 of the present invention.
Figure 9B:
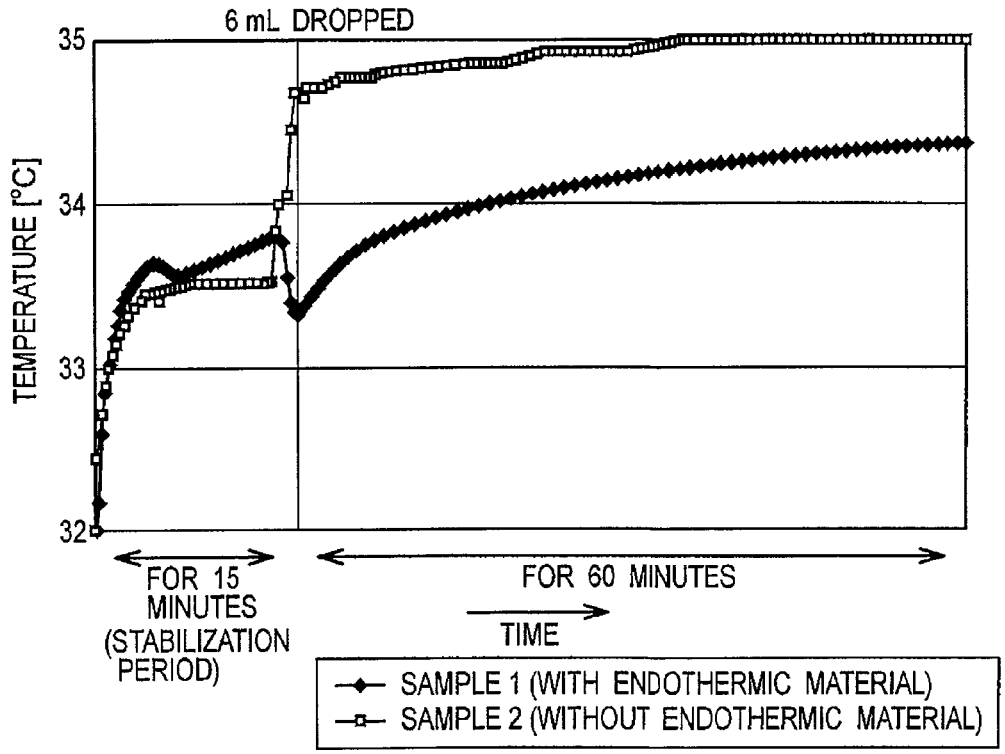
FIG. 9B is a graph that shows changes in temperature according to Example 1 of the present invention.

FIGS. 9A to 9B show measurement results of the temperature and humidity obtained by the above-mentioned evaluation test. FIG. 9A shows the measurement results of humidity, and FIG. 9B shows the measurement results of temperature.

As shown in FIGS. 9A to 9B, in Sample 2, the temperature and humidity sharply rose immediately after dropping. In contrast, the temperature and humidity Sample 1 rose less than those in Sample 2.

(Consideration Concerning Example 1)

The evaluation tests and evaluation results mentioned above showed that it is possible to suppress sharp increases in temperature and humidity in the space between the skin surface and the absorbent article, even when excretion of the body fluid is repeated, or even when a large amount of the body fluid is excreted. Since the temperature of the enclosed space does not reduce too much from the temperature at a blank, it also turns out that reduction in temperature is in a level which gives no uncomfortable feelings such as chilliness to the wearer.

As mentioned above, the absorbent article according to the present invention can suppress increases in temperature and humidity in the space between the skin surface and the absorbent article when the body fluid such as menstrual blood or urine is excreted. Accordingly, the absorbent article can suppress the stuffiness that the wearer feels.

Example 2

An evaluation test was conducted to obtain a backflow proportion of multiple top sheets having different shapes.

First, a test liquid was produced. The test liquid was produced in a same manner as in the case of Example 1. Moreover, an absorber was produced. The absorber was produced in a same manner as in the case of the absorber of Sample 2 in Example 1 mentioned above.

Next, several types of top sheets were produced as samples. Specifically, an air-through nonwoven fabric (30 gsm) having depressions and projections made by embossing was produced as Sample A. The depressions and projections in Sample A were formed by pressing an embossing roll on the nonwoven fabric. The depressions and projections in Sample A are formed approximately identical to the depressions 10*a* and projections 10*b* in the top sheet 10 shown in FIG. 2.

In Sample A, the depressions and projections were formed continuously in the longitudinal direction, and were alternately repeated in the width direction. Moreover, in Sample A, a height (from a bottom surface of a depression to a top surface of a projection) of the projection was 1.3 mm, and a pitch between projections adjacent to each other in the width direction was 2.1 mm.

Further, an air-through nonwoven fabric (35 gsm) was produced as Sample B, in which a basis weight of the projections (projections are solid) is larger than a basis weight of the depressions. The depressions and projections in Sample B are formed approximately identical to the depressions 11*a* and projections 11*b* in the top sheet 11 shown in FIG. 4.

Sample C was produced by stacking the above-mentioned Sample B on the intermediate sheet 91. The air-through nonwoven fabric of 38 gsm in which the high density regions and the low density regions are dispersed in the planar direction as shown in FIG. 6 was used as the intermediate sheet 91. A method for forming the high density regions and the low density regions is the same as that of the fifth embodiment.

Moreover, an air-through nonwoven fabric of 35 gsm in which no depressions and projections were formed was produced as Sample D.

Next, Sample A was placed on the produced absorber, and both sides thereof were joined by embossing in order to integrate Sample A and the absorber. As for Samples B to D, each sample was placed on the absorber and joined in the similar manner.

As a test device, only the acrylic lid used in Example 1 was used. Specifically, the acrylic lid into which two syringes 340 were inserted was used.

(Evaluation Method)

An evaluation test was conducted in accordance with the following method, using a product obtained by joining the absorber and Sample A. The evaluation test was conducted under environment of 35° C.±5° C. and 75 RH %±5 RH %.

First, 3 ml of the test liquid was poured into each of two syringes 340, and the syringes were installed in the acrylic lid. Next, the acrylic lid was disposed on the product obtained by joining the absorber and Sample A. The acrylic lid was disposed in the center in a planar direction of Sample A.

After disposition, the test liquid was dropped approximately simultaneously from the two syringes 340. The acrylic lid was removed after 1 minute from the start of dropping, and 10 sheets of filter paper (with a longitudinal dimension of 50 mm and a width dimension of 35 mm) were disposed on Sample A. Further, a weight adjusted to 60 g/cm$^2$ was disposed on the filter paper.

After 5 minutes from disposition of the weight, a weight of the filter paper was measured. Moreover, a backflow proportion of Sample A was calculated on the basis of a weight of 3 ml of the dropped test liquid and the weight of the test liquid attached to the filter paper. A ratio of the weight of the test liquid attached to the filter paper to the weight of the dropped test liquid was calculated as the backflow proportion.

Moreover, the above-mentioned evaluation tests were respectively conducted on Samples B to D in the similar manner, and each backflow proportion of Samples B to D was calculated.

(Evaluation Result)

Calculated results of each backflow proportion of Samples A to D are shown below. As shown in the following results, each of Samples A to C had a lower backflow proportion compared with that of Sample D.

Sample A: 7.4%
Sample B: 3.8%
Sample C: 1.1%
Sample D: 10.5%

(Consideration Concerning Example 2)

From the evaluation tests and evaluation results mentioned above, Samples A to C have a lower backflow proportion compared with that of Sample D. Namely, it turned out that Samples A to C cause backflow less frequently than Sample D does.

In this way, in Example 1, it turned out that the absorber provided with the endothermic material (potassium chloride) can suppress increases in temperature and humidity in an enclosed space. Moreover, in Example 2, it turned out that the top sheet having the depressions and projections formed therein can reduce backflow of the body fluid (test liquid) with a temperature lowered by the endothermic material, compared with the top sheet without the depressions and projections does.

Whole contents of Japan Patent Application No. 2008-140055 (filed on May 28, 2008) are incorporated herein by reference.

INDUSTRIAL APPLICABILITY

As described above, according to the present invention, it is applicable for an absorbent article and a sanitary napkin that can suppress the stuffiness that a wearer feels when the body fluid such as menstrual blood is excreted, and can reduce backflow of the body fluid having a temperature lowered.

What is claimed is:

1. An absorbent article, comprising:
a liquid permeable top sheet, a liquid impermeable back sheet, and an absorber interposed between the top sheet and the back sheet,
wherein
an endothermic material is disposed inside the absorber,
a depression and a projection are formed on a surface of the top sheet facing a human body, and
the endothermic material is disposed inside the absorber on a side facing the back sheet.

2. The absorbent article according to claim 1, wherein a basis weight of the projection is larger than a basis weight of the depression.

3. The absorbent article according to claim 1, wherein the surface of the top sheet has a plurality of depressions and a plurality of projections.

4. The absorbent article according to claim 3,
a height of the projections 0.3 to 15 mm, and
a pitch between adjacent projections of the top sheet is 0.5 to 30 mm.

5. The absorbent article according to claim 1, wherein a dimension of the endothermic material in a longitudinal direction of the absorbent article is 30-50% of a dimension of the absorber in the longitudinal direction of the absorbent article.

6. A sanitary napkin, comprising:
a liquid permeable top sheet, a liquid impermeable back sheet, and an absorber interposed between the top sheet and the back sheet,
wherein
an endothermic material is disposed inside the absorber, and
a surface of the top sheet has a plurality of depressions and projections on a wearer's skin, and
the endothermic material is disposed inside the absorber on a side facing the back sheet.

7. The sanitary napkin according to claim 6, further comprising a wing extending in a width direction of the absorber, wherein
in the sanitary napkin, a front region, a central region, and a rear region are provided continuously in a longitudinal direction of the absorber,
the endothermic material is disposed inside the absorber in an arrangement region including at least the central region of the sanitary napkin, and
a region of the central region in the longitudinal direction is a region in a longitudinal direction of the wing.

8. The sanitary napkin according to claim 6, wherein
in the sanitary napkin, an embossed groove is formed in both side portions in a width direction of the absorber,
the embossed groove is formed along a longitudinal direction of the absorber, and
the endothermic material is interposed between the embossed grooves.

9. The sanitary napkin according to claim 6, wherein
a height of the projections 0.3 to 15 mm, and
a pitch between adjacent projections of the top sheet is 0.5 to 30 mm.

10. The sanitary napkin absorbent article according to claim 6, wherein a dimension of the endothermic material in a longitudinal direction of the absorbent article is 30-50% of a dimension of the absorber in the longitudinal direction of the absorbent article.

* * * * *